US012558001B2

(12) United States Patent
Rigaux et al.

(10) Patent No.: US 12,558,001 B2
(45) Date of Patent: Feb. 24, 2026

(54) MUSCLE FATIGUE DETERMINATION METHOD

(71) Applicant: MYOCENE, Liège (BE)

(72) Inventors: Pierre Rigaux, Liège (BE); Jean-Yves Mignolet, Momalle (BE)

(73) Assignee: MYOCENE, Liège (BE)

( * ) Notice: Subject to any disclaimer, the term of this patent is extended or adjusted under 35 U.S.C. 154(b) by 1042 days.

(21) Appl. No.: 17/342,903

(22) Filed: Jun. 9, 2021

(65) Prior Publication Data

US 2022/0142508 A1      May 12, 2022

Related U.S. Application Data

(63) Continuation-in-part of application No. 17/091,468, filed on Nov. 6, 2020, now Pat. No. 11,864,898.

(30) Foreign Application Priority Data

Nov. 6, 2020    (BE) .................................. 2020/5792

(51) Int. Cl.
*A61B 5/11*         (2006.01)
*A61B 5/00*         (2006.01)
(Continued)

(52) U.S. Cl.
CPC ............. *A61B 5/1107* (2013.01); *A61B 5/103* (2013.01); *A61B 5/11* (2013.01); *A61B 5/22* (2013.01);
(Continued)

(58) Field of Classification Search
CPC ......... A61B 5/1107; A61B 5/22; A61B 5/224; A61B 5/1108; A61B 5/103; A61B 5/11;
(Continued)

(56) References Cited

U.S. PATENT DOCUMENTS 5,070,873 A     12/1991   Graupe et al.
6,236,890 B1 *   5/2001   Oldham ................. A61N 1/326
                                                   607/48
(Continued)

FOREIGN PATENT DOCUMENTS

CA          2765891 A1 * 12/2009   ........... A61N 1/0452
CN       103691059 A       4/2014
(Continued)

OTHER PUBLICATIONS

Douma, K. W. et al.; "Reliability of the Q Force; a mobile instrument for measuring isometric quadriceps muscle strength"; BMC Sports Science, Medicine and Rehabilitation; 2016; pp. 1-12; vol. 8, No. 4.

(Continued)

*Primary Examiner* — Jacqueline Cheng
*Assistant Examiner* — Jonathan E. Cooper
(74) *Attorney, Agent, or Firm* — CHRISTENSEN O'CONNOR JOHNSON KINDNESS PLLC

(57) ABSTRACT

A method for determining a muscle fatigue of a muscle includes the step of electrostimulating the muscle at different frequencies, wherein the electrostimulation includes, at each frequency, a repetition of pulses during a period of time lower than 5 s. The method further includes the steps of determining forces developed by the muscle in response to the electrostimulations of step (i); and determining a muscle fatigue on basis of the determined forces.

21 Claims, 2 Drawing Sheets

(51) Int. Cl.

| | | |
|---|---|---|
| *A61B 5/103* | (2006.01) | |
| *A61B 5/22* | (2006.01) | |
| *A61N 1/04* | (2006.01) | |

(52) U.S. Cl.
CPC . *A61B 5/68* (2013.01); *A61B 5/70* (2013.01); *A61B 2562/0261* (2013.01); *A61B 2562/0266* (2013.01); *A61N 1/0404* (2013.01)

(58) Field of Classification Search
CPC ..... A61B 5/68; A61B 5/70; A61B 2562/0261; A61B 2562/0266; A61B 2503/10; A61B 2505/09; A61B 2562/0247; A61B 5/4848; A61B 5/6891; A61B 5/702; A61B 5/4519; A61B 5/6828; A61B 5/6835; A61N 1/0452; A61N 1/36003; A61N 1/36034; A61N 1/0404
See application file for complete search history.

(56) References Cited

U.S. PATENT DOCUMENTS

| | | | | |
|---|---|---|---|---|
| 7,499,746 | B2 * | 3/2009 | Buhlmann | A61N 1/36021 607/2 |
| 9,114,255 | B1 | 8/2015 | Hartman et al. | |
| 9,878,152 | B2 * | 1/2018 | Kolen | A61B 5/389 |
| 2004/0039426 | A1 | 2/2004 | Hurtado | |
| 2005/0283204 | A1 | 12/2005 | Buhlmann et al. | |
| 2005/0283205 | A1 | 12/2005 | Lee et al. | |
| 2006/0270943 | A1 * | 11/2006 | Kamataki | A61B 5/389 600/554 |
| 2009/0319003 | A1 * | 12/2009 | Castel | A61N 1/36003 607/48 |
| 2010/0069796 | A1 | 3/2010 | Duncan et al. | |
| 2014/0058476 | A1 | 2/2014 | Crosby et al. | |
| 2014/0067010 | A1 * | 3/2014 | Sumners | A61N 1/36003 607/48 |
| 2017/0181689 | A1 * | 6/2017 | Lin | A61B 5/1107 |
| 2017/0209087 | A1 * | 7/2017 | Buhlmann | A61B 5/1107 |
| 2017/0340278 | A1 | 11/2017 | Imhauser | |
| 2017/0347941 | A1 | 12/2017 | Ejiri et al. | |
| 2018/0296831 | A1 * | 10/2018 | Matsushita | A61N 1/3603 |
| 2019/0022388 | A1 | 1/2019 | Stucke | |
| 2019/0223764 | A1 | 7/2019 | Hulvershorn et al. | |
| 2020/0179695 | A1 * | 6/2020 | Bergh | A61N 1/36034 |
| 2021/0370082 | A1 * | 12/2021 | Boll | A61B 18/12 |
| 2022/0331602 | A1 * | 10/2022 | Dzialecka | A61N 1/36014 |

FOREIGN PATENT DOCUMENTS

| | | | |
|---|---|---|---|
| CN | 107468255 | A | 12/2017 |
| CN | 110522999 | A | 12/2019 |
| CZ | 2018-559 | A3 | 3/2020 |
| JP | 4110771 | B2 | 7/2008 |
| JP | 5916154 | B2 | 5/2016 |
| KR | 101685013 | B1 | 12/2016 |

| | | | |
|---|---|---|---|
| WO | 1990/006152 | A1 | 6/1990 |
| WO | 2002/013696 | A1 | 2/2002 |
| WO | 2020/078486 | A1 | 4/2020 |

OTHER PUBLICATIONS

Edwards, R. H. T. et al.; "Fatigue of Long Duration in Human Skeletal Muscle After Exercise"; Journal of Physiology; Mar. 23, 1977; pp. 769-778; vol. 272.

Ruggiero, Luca et al.; "Prolonged low-frequency force depression is underestimated when assessed with doublets compared with tetani in the dorsiflexors"; Journal of Applied Physiology; Mar. 14, 2019; pp. 1352-1359; vol. 126; American Physiological Society.

Verkerke, G. J. et al.; "Precision, comfort and mechanical performance of the Quadriso-tester, a quadriceps force measuring device"; Medical & Biological Engineering & Computing; May 2003; pp. 283-289; vol. 41.

Chiu, Loren Z.F. et al., "The Fitness-Fatigue Model Revisited: Implications for Planning Short- and Long-Term Training," Strength and Conditioning Journal, Dec. 2003, pp. 42-51, vol. 25, No. 6, National Strength & Conditioning Association.

International Search Report and Written Opinion mailed Aug. 16, 2022, issued in corresponding International Application No. PCT/EP2022/061932, filed May 4, 2022, 16 pages.

Martin, V.; "Assessment of low-frequency fatigue with two methods of electrical stimulation"; Journal of Applied Physiology; Jul. 11, 2004; pp. 1923-1929; vol. 97; American Physiological Society.

Kirsch, Nicholas A., "Control Methods for Compensation and Inhibition of Muscle Fatigue in Neuroprosthetic Devices," Doctoral Dissertation, University of Pittsburgh; Mar. 21, 2016; 176 pages.

"Kyowa Load Cells Complete Catalog," Test Machines Australia, Aug. 2021, 59 pages, located at https://testmachines.com.au/wp-content/uploads/2021/08/Kyowa-Load-Cells-Complete-catalog.pdf.

Silva, Miguel T. et al., "An efficient muscle fatigue model for forward and inverse dynamic analysis of human movements," Procedia IUTAM, 2011, pp. 262-274, vol. 2, Elsevier Ltd.

Vollestad, Nina K., "Measurement of human muscle fatigue," Journal of Neuroscience Methods, 1997, pp. 219-227, vol. 74, Elsevier.

Zhang, Dingguo et al., "Cooperative Control for A Hybrid Rehabilitation System Combining Functional Electrical Stimulation and Robotic Exoskeleton," Frontiers in Neuroscience, Dec. 21, 2017, pp. 1-16, vol. 11.

Binder-Macleod, Stuart A; Halden, Esther E.; Jungles, Kimberly A., "Effects of stimulation intensity on the physiological responses of human motor units," Medicine & Science in Sports & Exercise, Apr. 1995, pp. 556-565.

Wang, H. et al., "An electrical muscle simulator based on functional electrical stimulation," 2012 IEEE International Conference on Robotics and Biomimetics (ROBIO), Guangzhou, China, 2012, pp. 1906-1911.

Zhang, Q. et al., "Torque prediction using stimulus evoked EMG and its identification for different muscle fatigue states in SCI subjects," 2010 Annual International Conference of the IEEE Engineering in Medicine and Biology, Buenos Aires, 2010, pp. 3523-3526.

* cited by examiner

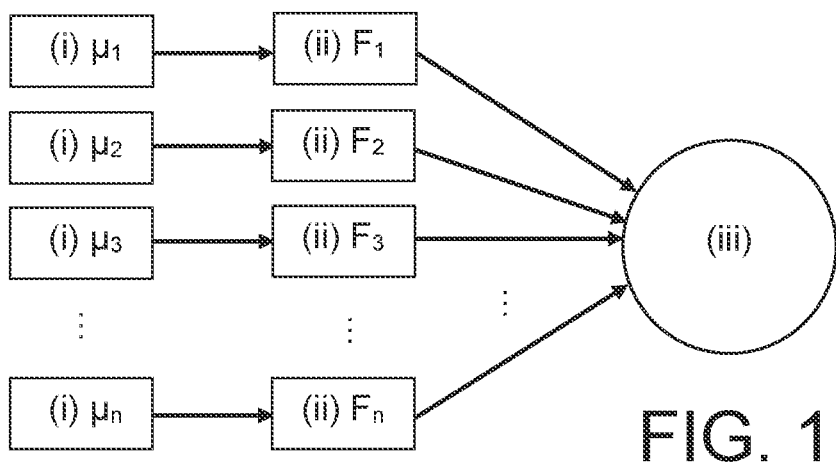
FIG. 1
FIG. 2
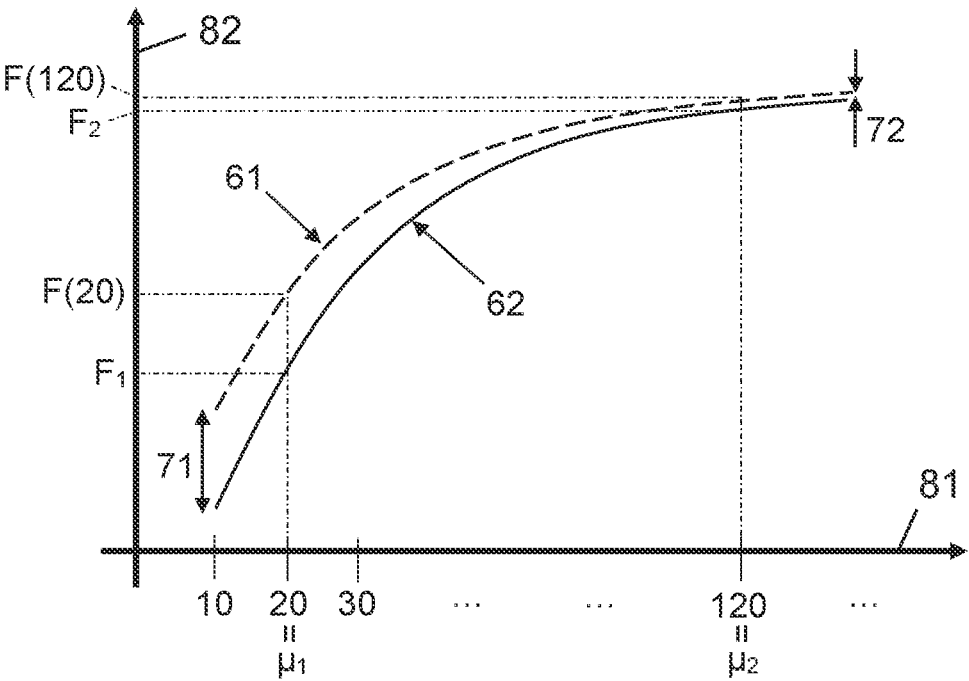

MUSCLE FATIGUE DETERMINATION METHOD

This application is a continuation-in-part of U.S. patent application Ser. No. 17/091,468, filed on Nov. 6, 2020, and also claims priority to Belgian application BE2020/5792, filed on Nov. 6, 2020, the disclosures of which are incorporated herein by reference.

TECHNICAL FIELD

The present disclosure relates to a muscle fatigue determination method.

BACKGROUND

Animal activities, in particular human activities, induce "fatigue". Such fatigue can be nervous (i.e. induced by intellectual or psychic activities) or physical (i.e. induced by physical work). A physical fatigue is also called a "muscle fatigue" because it results from a muscular work and leads to a decrease in the force that can be provided by the affected muscle(s). In particular, muscle fatigue can result in an incapacity to maintain and/or repeat a physical effort. As a consequence, the identification, measurement and/or monitoring of muscle fatigue play an important role, for example, in sport practices (e.g. for the purpose of training effectiveness optimization, injury prevention, individual sport training program conception, muscle readiness, . . . ), or in physiotherapy for muscle rehabilitation (e.g. for the purpose of exercise monitoring, treatment optimization, excessive treatment prevention, . . . ), and more generally in medicine.

A known method for assessing muscle fatigue of a subject is to perform a test requiring maximum voluntary contraction of said muscle (e.g. by voluntary movements), repeated several times. A muscle fatigue is deemed to have been identified if a predetermined maximal muscular force corresponding to a monitored data (time, speed, force, power, acceleration, . . . ) cannot be reached. The motivation of the subject for reaching a maximum contraction can however affect such muscle fatigue evaluation. Moreover, as this test induces itself an important muscle fatigue, it affects itself the results obtained by the method: it cannot be reproduced several times typically, and it cannot be performed after an intense muscle work (e.g. after a sport competition). In addition, this method has the drawback to put the subject at risk of injury. It is then desirable to develop an improved muscle fatigue determination method.

SUMMARY

An object of the disclosed subject matter is to provide a more efficient, safe and flexible method for determining a muscle fatigue. In particular, an object of the disclosed subject matter is to provide a method allowing the determination of a muscle fatigue without inducing itself muscle fatigue, independently of the subject will, at any time, without putting the subject at risk of injury.

For this purpose, the disclosed subject matter provides a determination method of a muscle fatigue of a muscle, comprising the following steps:

- (i) electrostimulating the muscle at different frequencies, the electrostimulation comprising, at each frequency, a repetition of pulses during a period of time lower than 5 s;
- (ii) determining forces developed by the muscle in response to the electro-stimulations of step (i);

- (iii) determining a muscle fatigue on basis of the forces determined at step (ii).

The method according to the present disclosure is more efficient, safe and flexible for determining the muscle fatigue than the method described in the prior art. In fact, the use of electrostimulations at steps (i) allows to stimulate the muscle whatever its fatigue and to make the muscle developing an involuntary force in response to the electrostimulations. This step can then be performed at any time, also after a sport training, without putting the subject at risk of injury, and it is not dependent on the subject will to urge a maximal contraction of the muscle. The limited period of time during which the pulses are repeated mitigates the risk of voluntary or reflex disturbance of the subject who can, otherwise, either increase the force by taking part with the electro-induced contraction, or on the contrary decrease it by contracting antagonist muscle to the electro-stimulated muscle. This renders the method more precise and efficient. The step (i) also does not induce muscle fatigue given that the number of electrostimulations are preferably limited and performed shortly, in order to observe muscle reactions and to determine the forces at step (ii). The muscle fatigue before and after an execution of the determination method is advantageously substantially the same.

This determination method allows to determine the muscle fatigue efficiently. Indeed, the inventors noticed that, as muscle fatigue deforms non-uniformly the curve of the force developed by the muscle in response to an electro-stimulation at a frequency as a function of this frequency, it was possible to determine the muscle fatigue at step (iii) on basis of a determination of this force for different frequencies, for example, by comparing muscle developed forces. This has the major advantage to be independent from the context of execution of the determination method. In particular, no comparison to a such standard known curve at rest for the subject, no preliminary measures, and no specific execution conditions are needed.

The determination method according to the present disclosure is convenient for a wide range of applications, in particular for determining muscle fatigue of sport professionals before, during or after a training or a competition, as well as muscle fatigue of injured and/or elderly people during muscle rehabilitation.

The determination method according to the present disclosure is particularly convenient for planning sport training. In this case, the method according to the present disclosure is preferably not applicable to a curative purpose and is not intended to identify or uncover a pathology. In this respect, the present disclosure can read as follows:

a method for planning a sport activity, comprising the following steps:

- (0) identifying a muscle to be stimulated during the sport activity;
- (i) electrostimulating the muscle at different frequencies, the electrostimulation comprising, at each frequency, repetition of pulses during a period of time lower than 5 s;
- (ii) determining forces developed by the muscle in response to the electro-stimulations of step (i);
- (iii) determining at least one muscle data information on basis of the forces determined at step (ii);
- (v) planning the sport activity on basis of the muscle data information.

Preferably, the sport activity is a sport training. Preferably, the muscle data information comprises (or optionally consists in) a muscle fatigue (data). Preferably, the method for planning a sport activity is non-curative and/or non-medical and/or non-therapeutic. Preferably, no curative diagnostic is derived at step (v), the latest being strictly of a planning nature. Preferably, the step (v) comprises (or optionally consists in) determining a time data depending on the muscle data information.

When the muscle data information comprises (or optionally consists in) a muscle fatigue (data), this sport activity planning method can be rephrased as comprising the following steps:

(0) identifying a muscle to be stimulated during the sport activity;
  (1) executing the determination method according to the present disclosure for determining a muscle fatigue of the muscle identified at step (0),
  (v) planning the sport activity on basis of the muscle fatigue determined at step (1).

In other words, the step (1) corresponds to the preceding steps (i) to (iii).

More generally, the determination method according to the present disclosure, can also consists in a non-curative and/or non-medical and/or non-therapeutic determination method of a muscle fatigue of a muscle, comprising the steps (i) to (iii). Preferably, in this case, no curative diagnostic is derived from step (iii) and/or, in other words, any curative diagnostic deduction step from the muscle fatigue determined at step (iii) is excluded from the method.

Any of the following embodiments and advantages of the determination method according to the disclosed subject matter as generically stated at the beginning of the present disclosure applies mutatis mutandis to the specific particular case of the method above disclosed, in particular to the sport activity planning methods and any non-curative embodiments. In particular, it will be understood by a skilled person that any of the embodiments presented in the claims can be considered alone or in combination with these methods.

Another advantage of the determination method of the disclosed subject matter is that it allows for a determination of specific muscle fatigues. Indeed, the muscle fatigue depends on many physiologic factors. In particular, the muscle fatigue can be caused by a deficiency of a neuromuscular neurological control when the latter cannot stimulate the muscle fibers to a maximum potential (leading to a so-called "central muscle fatigue"), or by alteration of the contraction force at direct level of the muscle fibers (leading to a so-called "peripheral muscle fatigue"). In the framework of the present disclosure, the determination method allows to determine directly at step (iii) the peripheral muscle fatigue given that the electrostimulations of step (i) affect directly of the peripheral muscle fibers, independently from the central neurological control of the muscle contraction. Step (iii) can nevertheless optionally also comprise a central muscle fatigue determination substep by subtraction of the determined peripheral muscle fatigue from another global fatigue measurement. This distinctive muscle fatigue determination is new with regard to the prior art methods.

Moreover, the peripheral muscle fatigue comprises itself two kinds of muscle fatigues depending how long the muscle fatigue affects the muscle: the so-called "short-lasting peripheral muscle fatigue" that is essentially linked to energetic and/or metabolic factors, from which it can be recovered quickly (some minutes), and the so-called "long-lasting peripheral muscle fatigue" that persists for several hours and even several days (e.g. after a physical effort). The peripheral muscle fatigue determined at step (iii) is preferably and more specifically a long-lasting peripheral muscle fatigue. Optionally, a short-lasting peripheral muscle fatigue can also be determined at step (iii) by additional determination of the muscle fatigue in an interval of time following the method of the present disclosure, and subtraction of the obtained results.

In the framework of the present disclosure, the term "electrostimulation" and any of its variants preferably refer to neuromuscular electrical stimulation or any kind of stimulation of the motor neurons of the tested muscle. Such stimulation is preferably performed by a stimulator comprising a generator of electric pulses and electrodes adapted for being placed on the skin of the subject, at proximity and/or beside the muscle, and connected to the generator in such a way that a current can be transmitted to the muscle by the electrodes. The intensity and the frequency of the electric pulses can be adjusted. Such generator and electrodes are well known by a skilled person.

Preferably, the period of time of pulses repetition is lower than 500 ms. This shorter period of time makes it possible, in addition to aforementioned advantages, to reduce the overall time of application of the method. This mitigates even more the risk of voluntary or reflex disturbance of the subject. The period of time of pulses repetition is preferably lower than 250 ms and more preferably, the period of time is between 100 ms and 250 ms, included. Preferably, the period of time is between 150 and 250 ms, more preferably, it is about 150+x ms, for an x integer comprised between 0 and 100, e.g. 150, 160, 170, 180, 190, 200, 210, 220, 230, 240 or 250 ms.

Any of the above-mentioned periods of time that is lower than 250 ms makes it possible, in addition:

on one hand, to reach a maximum force generated by the electro-induced contraction, and,
  on the other hand, that this maximum force is exclusively due to the electro-induced contraction without any disturbance linked to a voluntary or reflex reaction of the subject.

The absence of voluntary or reflex disturbance makes it possible to obtain precise measurement of the force resulting solely from the electro-induced contraction. This accuracy of the recorded force allows therefore a good measurement of muscle fatigue.

In other words, these advantageous periods of time allow to provide a number of pulses at each (selected) frequency to the muscles that allows to reach the maximal force developed by the muscles in response to the pulses at this frequency (and to determine it at step (ii)) in a sufficiently short period of time avoiding to incur muscle fatigue and/or for the patient to provide any voluntary force.

These periods of time discovered by the inventors are then a good compromise between this two contradictory constraints; the first one inducing a need for a sufficiently long period of time and the second one inducing a need for a sufficiently short period of time.

It can be pointed out that an exact time period data T (in seconds) is equivalent to an exact number N of pulses data at a given frequency $\mu$ (in Hz). Those numbers are in fact satisfying the formula $T=N/\mu$.

Preferably, for each frequency, the pulses are repeated between 2 and 50 times and, more preferably, for each frequency, the pulses are repeated between 5 and 20 times, included. This range of repetitions of the electrical stimulating pulse makes it possible to reach the maximum strength. The force recorded is maximal and therefore allows a correct and precise measurement of the state of muscle fatigue.

According to a representative embodiment of the disclosed subject matter, a first rest period, that is preferably comprised between 100 ms and 10 s, occurs between two electrostimulations at different frequencies at step (i). Preferably, the first rest period is comprised between 115 ms and 5 s, more preferably again between 300 ms and 1 s included.

A rest period between two electrostimulations at different frequencies at step (i) makes it possible to mitigate or even avoid the disturbance form an electrostimulation to another electrostimulation, that can be due for instance to a muscular tetanisation.

The upper bound of 10 s allows a reasonable duration of the overall application time of the method. Preferably, the upper bound of 5 s makes it possible to quickly perform the method. Lastly, the upper bound of 1 s is a balance between an efficient rest period duration and an overall application duration of the method.

The lower bound comprised between 100 ms and 115 ms makes it possible to measure a force data at an electrostimulation at another frequency at step (i) that is sufficiently little affected by the electrostimulation at previous frequency to deduce and/or determine a corresponding maximal force at step (ii) with a certain margin of error.

The lower bound comprised between 115 ms and 300 ms is preferable because it allows enough time for the muscle to return to normal or relaxed conditions (in particular, without any contraction or residual force developed) between the electrostimulation at two different frequencies at step (i). This allows to determine directly the (maximal) force developed by the muscle at each of these frequencies without determination disturbances. In particular, no deduction with significant margin error and no intermediate measurements and/or calculations would be needed as for a first rest period below 115 ms.

When the muscle has a certain level of muscle fatigue, a phenomenon described as "slowing of relaxation" can take place. When it is present, this phenomenon prolongs the muscular response from an electrostimulation at a frequency to another electrostimulation at another frequency at step (i) and therefore disturbs the measurement of the muscular response at said another electrostimulation at another frequency during step (i). Advantageously, even if this phenomenon happens, a first rest period higher than 115 ms allows to determine correctly the force developed by the muscle in response to each of the electrostimulation by applying any appropriate mathematical or computer implemented treatment configured for deleting the "slowing of relaxation" disturbance. In fact, as this phenomenon is known, it is predictable in a certain measure and can be taken into account at step (ii). An exemplary treatment to implement would simply be a linear interpolation of the expected disturbance and its removal from a measured force.

The lower bound being greater than 300 ms is nevertheless preferred because it always allows a full return to normal and/or relaxed conditions for the muscle between two consecutive electrostimulations at step (i). In this case, no disturbance affects the measurement of muscle response triggered by said electrostimulation at another frequency.

Values such as ½, ⅗, ⅘, 1, ⁶⁄₅, ⅞, 8/5, 9/5 seconds for the first rest period are preferred because:

on one hand they are further enough from any of the other lower bounds, then certainly avoiding any potential disturbances of the force determination at step (ii) between two consecutive electrostimulation at step (i), and on the other hand, they are short enough (at the scale of the human perception) to make the overall method sufficiently short and easily applicable in an overall short period of time.

According to an embodiment, the step of electrostimulating at step (i) is performed at a given electric charge, and wherein the method comprises the step:

(iv) repeating steps (i), (ii) and (iii) a number of times with increasing electric charge, the electric charge at step (i) being increased by a charge step between two occurrences of step (i).

The step (iv) allows to obtain a range of determinations (e.g. measures) of the muscle fatigue and then make sure that the muscle fatigue is correctly determined with an advantageous extremely low error margin. Nevertheless, this embodiment makes necessary to deal with another phenomenon as it is introduced below.

This embodiment of the disclosed subject matter mitigates or even avoids a known muscular physiological phenomenon called "Potentiation" (or Post-Activation-Potentiation, or staircase phenomenon, or posttetanic potentiation) described in the scientific literature on muscular physiology. This phenomenon is defined as the effect of prior muscular activity on the enhancement of subsequent muscle contraction. Thus, muscle activity produces muscle fatigue and also potentiation, which is the opposite phenomenon to peripheral muscle fatigue. Potentiation therefore coexists with muscle fatigue and can more or less compensate for it. This phenomenon of potentiation is obtained with all types of muscular activity. Therefore, when performing muscle electrostimulation in order to determine muscle fatigue, the electro-induced muscle contraction generates a potentiation of the stimulated muscle fibers which masks muscle fatigue and disturbs its determination. This disturbance is all the more important as the electrical stimulation pulses are numerous and repeated within a determined period of time. Therefore, increasing the electric charge at step (i) by a charge step between two occurrences of step (i) according to the present disclosure makes it possible to perform series of electrostimulations (i.e., two or more occurrences of step (i)) at different frequencies on layers (or strata) of muscle fibers that are not always the same at each occurrence of step (i). Each occurrence of step (i) makes it possible to involve new fibers that are not yet potentiated by previous stimulation episodes.

During a given application of step (i), making it possible to have the ratio of two or more maximum forces, the fibers subjected to the electrostimulations at different frequencies are not potentiated yet. Then, a higher electric charge at a subsequent occurrence of step (i) recruits an additional layer of muscle fibers which are therefore not potentiated by the previous occurrence of step (i). Thus, by increasing the electric charge at each occurrence of step (i), the spatial recruitment of muscle fibers is modified, and new fibers are involved that are not yet potentiated by the previous occurrences of step (i).

Preferably, the electric charge is defined by the electric intensity of the pulses, and/or by the (individual) pulse duration. In the following description of the disclosed subject matter, it is preferably only defined by the electric intensity of the pulses. Nevertheless, this does not exclude other kind of "electric charge" from the scope of the present disclosure.

According to an embodiment, the electric intensity for a constant pulse duration is increased between 10 and 100 mA, and/or the number of times being comprised between 5 to 30, and/or the charge step corresponds to an intensity increasing comprised between +0.1 and +10 mA. Preferably, these "and/or" are "and".

In this case, the constant pulse increases from a lower value to an higher value, both between 10 and 100 mA.

Preferably, the lower value is comprised between 10 and 40 mA, more preferably, it is about 25 mA, in order to have a very smooth first electrostimulation feeling for the subject. Preferably, the higher value is between 30 and 60 mA, more preferably, it is about 40 mA, in order to avoid too high stress for the muscle. Preferably the number of times is comprised between 10 and 20, more preferably again it is about 15, in order to obtain enough determinations (e.g. measures) of the muscle fatigue and then to have a very low error margin from the method. Preferably, the charge step is an intensity increasing between +0.5 and +5 mA, more preferably it is about +1 mA, such step values being sufficient for electrostimulating enough different muscular fibers from one occurrence of steps (i), (ii) and (iii) to the other.

Preferably, the electric intensity is increased from 25 to 40 mA with 15 charge steps of +1 mA. Such an increase in intensity makes it possible to recruit each time a new layer of muscle fibers which is not affected by the electrostimulations of the previous occurrence of step (i) and is therefore not potentiated. This renders the determination method even more precise and easy to implement.

A similar increase in voltage has the same effect, or an increase in pulse width for a fixed electrical current.

According to an embodiment, a second rest period occurs between two occurrences of step (i). Thanks to the second rest period, potentiation is even more mitigated or avoided because the number of electrical impulses per unit of time is reduced when occurrences of step (i) are temporally spaced apart. Thus, the greater the time duration between repeated episodes of stimulation, the less potentiation on the muscle fibers recruited by the episodes of stimulation. However, similarly to the first rest period, the second rest period should not last too much for avoiding to render the execution of the method too slow and inapplicable.

The inventors have determined a good compromise between these two opposite constraints for the definition of the second rest period between two occurrences of step (i). Preferably, this period is comprised between 100 ms and 5 minutes, included, which allow to limit the potentiation and the time of execution of the method. Better range are more preferably given by a second rest period comprised between 145 ms and 10 s, preferably between 330 ms and 5 s included. The magnitude of the potentiation depending on the number of electrical pulses delivered in a defined period of time, the disclosed subject matter is advantageous in order to limit potentiation by reducing the number of pulses per unit of time when repeating step.

The second rest period lasting between 145 and 330 ms gives enough time for the muscle to return to normal or relaxed conditions (then, without contraction or residual force developed) between two occurrence of step (i). This allows to determine directly the (maximal) force developed by the muscle in response to each electrostimulation without disturbances. In particular, no deduction with significant margin error and no intermediate measurements and/or calculations would be needed, which is not the case for a second rest period between 100 and 145 ms. Even if a slowing of relaxation phenomenon of the muscle happens, a second rest period higher than 145 ms allows to determine correctly the force developed by the muscle in response to each of the electrostimulation by applying any appropriate mathematical or computer implemented treatment configured for deleting the "slowing of relaxation" disturbance, as discussed above with regard to the first rest period. Of course, in both cases, such treatment is preferably part of step (ii).

A second rest period greater than 330 ms is nevertheless preferred because it always allows a full return to normal and/or relaxed conditions for the muscle between the end of an occurrence of step (i) and the beginning of the next occurrence of step (i) through step (iv). In this case, no disturbance affects the measurement of muscle in response to the electrostimulations.

Values such as 1, 2, 3, 4 or 5 seconds for the second rest period are highly preferred because, on one hand, they are further enough from any of the above-mentioned lower values, and then certainly avoid disturbances of the force determination at step (ii) between two consecutive occurrences of step (i), and on the other hand, they are short enough (at the scale of the human perception) to make the execution of the overall method sufficiently fast and easily applicable.

In brief, these embodiments of the disclosed subject matter minimize the potentiation so that the measurement of muscle fatigue is accurate and not altered or underestimated due to the potentiation caused by the electrostimulation. This potentiation is all the more important as the stimulations are repeated and the number of pulses high.

Preferably, a first rest period occurs between two electro-stimulations at different frequencies at step (i), the first rest period being lower than a second rest period that occurs between two occurrences of step (i). The second frequency is preferably greater than the first frequency, the muscle response level being also higher at the second frequency. Therefore, it is preferable to wait a greater time after the application of the electrostimulation at the second frequency in order to ensure mitigation or even extinction of muscle response following last electrostimulation. For example, the first rest period is about 1 second, and the second rest period is about 5 seconds.

According to an embodiment, the determination method comprises, before step (i), a preliminary electrostimulating step of the muscle with an isolated pulse, and wherein a third rest period comprised between 100 ms and 10 s occurs between this preliminary electrostimulating step and step (i).

This optional isolated pulse is advantageous for measuring muscular data information such as an amplitude of the initial muscular response to the pulse, and/or a contraction speed, and/or preliminary potentiation data, . . . . This can be used, for example, in order to adapt the pulse electric intensity to the subject (or to the muscle), or generally, in order to provide a more personal execution of the method to the subject.

Preferably, according to the embodiments comprising a repetition step (iv), the preliminary electrostimulating step is repeated before each execution of step (i). This allows to gather such muscular data information continuously during the execution of the method and/or potentially to adapt this execution. Alternatively, this preliminary electrostimulating step can be executed only once at the beginning of an overall execution of the method.

The third rest period is preferably similar to any of the first and second rest periods. The above discussion for any of these rest period can apply for the third rest period. In particular, the latest is preferably about 1 second.

In the framework of this document, the use of the indefinite article "a", "an" or the definite article "the" to introduce an element does not exclude the presence of a plurality of these elements. In this document, the terms "first", "second", "third" and the like are solely used to differentiate elements and do not imply any order in these elements. In this document, the terms "at level of" and "at the level of" are used equivalently. In the framework of this document, the terms "on basis of" and "on the basis of" are used equivalently. The latter are not limitative: the fact that a first quantity is determined on basis of a second quantity do not exclude that the first quantity can also be determined on basis of a third quantity together with the first quantity.

In the framework of the present document, the terms "smaller than", "lower than" and "less than" are to be interpreted similarly as the mathematical symbol "≤", and the terms "greater than" and "higher than" are to be interpreted as the mathematical symbol "≥". Additionally, the use of the verbs "comprise", "include", "involve" or any other similar variant, as well as their conjugational forms, cannot exclude the presence of elements other than those mentioned. When the verb "comprise" is used for defining an interval by the terms "comprised between" two values, these two values should not be interpreted as excluded from the interval.

In the framework of this document, the use of terms "preferable," "preferably," "preferred," and the like should not be considered as limiting with respect to the scope of the disclosed subject matter or in regard to claim interpretation. More specifically, the inclusion of a "preferred" limitation or embodiment in the disclosure is not intended to limit the scope of claimed subject matter to only include the "preferred" embodiments. In this regard, the inclusion of "preferred" embodiments should not be interpreted to signal the surrender of subject matter not identified as such.

Preferably, the frequencies are comprised between 0 and 1000 Hz, more preferably smaller than 500 Hz, more preferably, smaller than 200 Hz. The frequencies can be comprised between 5 and 150 Hz. Such bounds allow to avoid muscle fatigue induction by an execution of the determination method.

According to a representative embodiment of the determination method, the frequencies of step (i) are comprised between 0 and 500 Hz, preferably, between 0 and 200 HZ, and comprise (and optionally, consists in):

a first frequency, and a second frequency greater than the first frequency, the first frequency differing from at least 10% of the second frequency (in the sense that: if $\mu_1$ and $\mu_2$ are the first and second frequencies, $\mu_2 - \mu_1 \geq \mu_2/10$).

In this case, the forces determined at step (ii) comprises a first force developed by the muscle in response to the electrostimulation of step (i) at the first frequency, and a second force developed by the muscle in response to the electrostimulation of step (i) at the second frequency. Each of these forces preferably corresponds to a maximal force developed in response to a whole repetition of pulses at the corresponding frequency (this repetition constituting then one electrostimulation at this frequency). The difference of at least 10% between the first and second frequencies is advantageous in order to ensure that at least two points (frequency used at step (i), force determined at step (ii)) on the aforementioned curve are sufficiently spaced one from the other for performing more efficiently step (iii). This allows to take all advantage of a non-uniformity and non-linearity of the deformation of the curve in function of a preexisting muscle fatigue given that the forces developed by the muscle in response to electrostimulations at low frequencies, e.g. between 0 to 50 Hz, is more affected by this muscle fatigue than the forces developed by the muscle in response to electrostimulations at higher frequencies, as illustrated in FIG. 2 hereafter introduced.

In particular, the above-mentioned difference is preferably at least 20%, more preferably at least 50%. Preferably, the first frequency is comprised between 0 and 50 Hz and/or the second frequency is comprised between 50 and 200 Hz. Preferably, the first frequency is about 20 Hz and/or the second frequency is about 120 Hz. Any other similar couple of values for the first and second frequencies can be used, for example: 10 and 50 Hz, 30 and 80 Hz, 50 and 150 Hz, etc.

More preferably, according to the above-mentioned embodiment, the different frequencies of step (i) consist in the first and second frequencies and the forces determined at step (ii) consist in the first and second forces. Advantageously, it is possible to determine the muscle fatigue at step (iii) only by considering these two (maximal) forces. It will be explained hereafter.

The advantage is to avoid muscle fatigue induction by limiting the electrostimulations at step (i) in number and frequency. Another advantage is to facilitate the execution of step (iii) by considering only a limited number of data. The disclosed subject matter however is not limited to different frequencies consisting in only the first and second frequencies. Other numbers than two frequencies can be considered. As an example, the different frequencies (and associated forces determined at step (ii) can be three, four, five, six, seven, eight, nine, ten or more frequencies, and those can also be equidistant in a range of frequency, such that those defined previously.

According to an example of a representative embodiment of the disclosed subject matter the determination method comprises at step (i)

electrostimulating the muscle with a repetition of 3, 4, 5, or 6 pulses at the first frequency of about 10, 15, 20 or 25 Hz;

electrostimulating the muscle with a repetition of 16, 17, 18 or 19 pulses at the second frequency of about 100, 110, 120 or 130 Hz;

during the period of time comprised between 100 and 250 ms. This is advantageous in order to have a number of repetitions of the electrical pulses which makes it possible, on one hand, to reach (and determine) the maximum force generated by the electro-induced contraction, and, on the other hand, that this maximum force is exclusively due to the electro-induced contraction without any disturbance linked to a voluntary or reflex reaction of the subject. At the same time, this produces little or almost no potentiation of the muscle fibers of the tested muscle (different layers of muscle being stimulated) and makes it possible to measure efficiently muscle fatigue.

Preferably, in the context of a first frequency and a second frequency greater than the first frequency, step (iii) comprises a computation of a ratio of the first force to the second force, the muscle fatigue being determined on basis of this ratio. More specifically and preferably, step (iii) also comprises a comparison of the computed ratio to a threshold, and a determination of the muscle fatigue based on this comparison of the computed ratio to the threshold. This implementation of step (iii) is very simple and allows a fast and low complexity computation for determining the muscle fatigue. It is also very efficient. Indeed, as it is explained previously, as the first frequency differs from at least 10% of the second frequency, the ratio is fully affected by the non-uniformity of the curve deformation in function of the muscle fatigue. As a consequence, when the above-mentioned comparison allows to identify a difference between the computed ratio and a threshold corresponding to an expected ratio for a non-fatigued muscle, such difference expresses a muscle fatigue that can then be determined at least implicitly and preferably explicitly.

This embodiment of the disclosed subject matter, and the term "on basis of" does not exclude a step (iii) that would also take into account other information or computations derived from the forces determined at step (ii). For example, at least another computation on other forces determined at step (ii) can be used for determining the muscle fatigue, and step (iii) can comprise a substep for averaging the muscle fatigue determined in this way, and by the comparison of the computed ratio to the threshold, which allow a more precise and efficient determination of the muscle fatigue as an average of such determinations. For example, this at least another computation can comprise a ratio computation of a third force to a fourth force among the forces determined at step (ii).

As a generalization of the preceding embodiments of the disclosed subject matter, step (iii) preferably comprises a comparison of the forces determined at step (ii), and a determination of the muscle fatigue based on this comparison of the forces.

The aforementioned threshold to which a ratio of the first force to the second force is compared, consists preferably in a number $F(\mu)/F(\mu')$, where:

F is a human independent increasing regular function expressing a force developed by a non-fatigued muscle in response to an electrostimulation as a function of a frequency of this electrostimulation;

$\mu$ and $\mu'$ are respectively the first and the second frequencies.

In other words, in this case, F is preferably a skilled person known theoretical function, underlying a family of thresholds of the form $F(\mu)/F(\mu')$ that can be used for defining the threshold.

Expressing the ratio in this way is advantageous because it is human independent and indirectly given through the function F for any couple of the first and second frequencies. This embodiment is not limitative of the scope of the present disclosure. It is not necessary to consider a whole function F for the above-mentioned embodiment involving only the first and the second frequencies, as a number corresponding to these frequencies is sufficient.

In the context of computing a ratio between frequencies and comparing it to a threshold:

the first frequency is preferably comprised between 10 and 40 Hz; and/or the second frequency is preferably comprised between 90 and 130 Hz.

In this case, the threshold is preferably comprised between 40 and 90%. More preferably, the first frequency is about 20 Hz, the second frequency is about 120 Hz, and the threshold is about 60%, or 65%, or 70%, or 75%, or 80%. Such a combination of values makes it very easy and efficient to implement the determination method of the present disclosure in the context of a first frequency and a second frequency greater than the first frequency. It does obviously not limit the scope of the disclosed subject matter, and other values can be considered.

In the framework of the present document, the terms "determining", "determine", "determination" and any other variants correspond preferably to the terms "quantifying", "quantify" and "quantification" in the sense that the muscle fatigue is preferably not just identified but explicitly measured and/or computed. For example, in the preceding embodiments, an explicit measure and/or computation can be derived from the comparison of the computed ratio to the threshold and/or from determined muscle fatigue averaging. The scope of step (iii) nevertheless preferably does not exclude a determination of the muscle fatigue based on other physical quantities at least partially derived from the forces determined at step (ii), such as, for instance, associated torques. Reciprocally, the scope of step (ii) preferably does not exclude a determination of the forces based on intermediate physical quantities related to the forces that can be measured in response to the electrostimulations of step (i), such as, for instance, displacements, accelerations, and/or torques.

According to other embodiment of the determination method of the present disclosure, the frequencies comprise a minimal frequency smaller than 50 Hz, and a family of frequencies smaller than 200 Hz and integer multiple of the minimal frequency. This family comprises more preferably all the frequencies smaller than 150 Hz and integer multiple of the minimal frequency. In other words, in this case, the frequencies of this family are equidistant. Although this embodiment requires more electrostimulations at step (i), it is advantageous because it allows to acquire more data among which at least some underlie a wide variety of points (frequency used at step (i), force determined at step (ii)) at least locally, preferably globally, uniformly distributed on the aforementioned curve for performing efficiently and precisely step (iii). Such a family can for example consists in $\{5n\ Hz | 1 \leq n \leq 30, n\ integer\} = \{5\ Hz, 10\ Hz, 15\ Hz, \ldots, 150\ Hz\}$ for 5 Hz being the minimal frequency, or $\{30\ Hz, 60\ Hz, 90\ Hz, 120\ Hz\}$ for 30 Hz being the minimal frequency. The family can also be for example $\{10\ Hz, 20\ Hz, 30\ Hz, 40\ Hz, 100\ Hz, 110\ Hz, 120\ Hz, 130\ Hz\}$ for 10 Hz being the minimal frequency, all the frequencies integer multiple of 10 Hz being then not comprise within the family.

Preferably, according to the preceding embodiment of the method, step (iii) comprises:

a computation of a discrete integral of a (discrete) function associating, to each frequency of the family, a force determined at step (ii) developed by the muscle in response to the electrostimulation of step (i) at this frequency;

a determination of the muscle fatigue based on the computed discrete integral.

This discrete integral corresponds typically to a Riemann sum. It is preferably efficiently performed when the family comprises all the integer multiple of the minimal frequency smaller than 150 Hz, the latter being preferably smaller than 20 Hz, more preferably smaller than 10 Hz, for a good computation precision. Preferably, step (iii) comprises a comparison of the computed discrete integral to an area value, and a determination of the muscle fatigue based on this comparison of the computed discrete integral to the area value. This area value is preferably a value of the area under the graph of the aforementioned function F. As well known in discrete calculus, the comparison allows to evaluate a difference between this theoretical area for a non-fatigued muscle and its approximations by a Riemann sum for the muscle, and to determine the muscle fatigue on this basis in a precise way because of the number and preferred global uniform repartition of the frequencies of the family. Optionally, the different frequencies consist in this family of frequencies.

Embodiments of the preceding paragraphs are compatible with various of the other preceding embodiments. In particular, as explained, it is possible to consider a muscle fatigue determination at step (iii) based on a computed ratio between the first and the second frequencies and on an aforementioned computed discrete integral, for example by an averaged comparison of the computed ratio and the computed discrete integral to human independent expected normal values for a non-fatigued muscle. In this case, the first and second frequencies can also belong to the family.

According to another embodiment of the method of the present disclosure fully compatible with the preceding embodiments, the forces are determined in steps (ii) by direct force measurements, preferably by means of a strain gauge or a dynamometer. In particular, the determination of the forces at step (ii) is done directly, by measuring forces (in Newton), by appropriate technologies and not by intermediate or indirect measures and/or observations (such as by electromyography) nor deduction or estimation inducing a risk of error in step (ii). These direct force measurements are preferably performed by a new and dedicated device introduced hereafter as part of a system of the present disclosure.

Preferably, the muscle involved in the disclosed subject matter consists in a muscle of a lower limb of a human. Preferably, this muscle consists in the quadriceps or the hamstring. In any of these cases, according to a representative embodiment of the present disclosure, the method comprises the following steps before step (i):

(a) providing a device comprising:
        a seat for receiving the human in a seated position, and adapted for being positioned on a horizontal support;
        a leg support element mechanically coupled to the seat, and adapted for receiving at least part of a leg of the lower limb;
        a measuring instrument for measuring the (above-mentioned) forces at level of the leg support element;
    (b) positioning the seat on a horizontal support;
    (c) positioning the human on the seat, in a seated position; and
    (d) positioning at least part of the leg on the leg support element.

Preferably, the forces are determined at step (ii) by means of this measuring instrument. This device is advantageously very simple and easy to move, while allowing to determine precisely the forces at step (ii). The process for executing step (i) is also very simple as the human is seated on the seat, his leg being simply positioned and preferably maintained in the leg support element. Preferably, the weight of the human exerted at level of the seat allows simply the device to remain substantially stationary with respect to the horizontal support during an execution of steps (i) and (ii). In particular, no complex structure is needed for receiving the human and executing the method of the present disclosure. A simple plane coupled to the leg support element can be used as seat and positioned on a horizontal support such as a table or another seat, anywhere. The device is fully detailed hereafter as part of a muscle fatigue determination system of the present disclosure.

Preferably, above-mentioned steps (c) and (d) are such that:
    a foot of lower limb hangs in an air; and/or, preferably and,
    a whole thigh of the lower limb lies on the seat; and/or, preferably and,
    a back of a knee of the lower limb is in contact with a lateral side of the seat.

Advantageously, the seat is the only contact point of the lower limb (at a seat front surface level for the thigh and at a seat lateral surface level for the knee) which allows to know perfectly the measurement conditions of the forces at step (ii) and to avoid any measure perturbation that could be induced by a force exerted by the foot on a support, for instance on the ground. Preferably, the human is positioned at steps (b) and (c) such that its back is straight and form a substantially right angle with the lower limb thigh. Thanks to the simple structure of the device and the easy positioning of the human, the measures of the forces by the measuring instrument are reproducible. This is very advantageous for the purpose of applications of the determination method of the present disclosure given that muscle fatigue determined at step (iii) can be compared from one day to another, whenever and wherever, provided that the seat can be positioned on a horizontal support, without the necessity of executing the determination method in the same place and in the same conditions, and without taking care of a multiplicity of positioning parameters of the human.

It is preferable to implement the determination method according to the present disclosure on a system that makes it possible to efficiently determine a muscle fatigue without inducing itself muscle fatigue, independently of the subject will, at any time, without putting the subject at risk of injury.

For this purpose, such a system for implementing the muscle fatigue determination method of a muscle preferably comprises:
    a stimulator for generating an electrostimulation of the muscle at a range of frequencies, and comprising a controller for selecting:
        any frequency of electrostimulation in the range of frequencies, and/or
        any number of pulses, and/or
        any repetition of pulses during a period of time, or any such time period, and/or
        any first and/or second and/or third rest periods respectively between electrostimulations at different frequencies at step (i), and/or between consecutive occurrences of step (i), and/or between a preliminary electrostimulating step and step (i)
        as described above in relation to the method;
    a device for determining a force developed by the muscle in response to an electrostimulation generated by the stimulator;
    a logical unit connected to the device, and configured for determining a muscle fatigue on basis of forces determined by the device as forces developed by the muscle in response to electrostimulations generated by the stimulator at different frequencies of the range of frequencies.

The stimulator, and more specifically the controller, is also preferably configured for allowing to select and/or to modify (in particular, increase) the electric charge, preferably the pulses electric intensity, between two occurrences of step (i), with certain charge step as described previously. According to the above-described relevant embodiments of the method, the controller allows preferably for a selection of any electric charge related parameters such as: the pulse electric intensity, and/or the pulse duration, and/or the number of repetitions of steps (i) to (iii) implemented in step (iv), and/or the charge step between two occurrences of step (i). More preferably, the controller can be programmed to implement an electric charge program related to the method for reproducing the progressive increasing of the electric charge associated to the electrostimulations as describe previously, and/or the frequency selection.

The above-mentioned system allows for executing the determination method according to the present disclosure. Preferably, the step (i) is implemented by the stimulator, the step (ii) is implemented by the device, and/or the step (iii) is implemented by the logical unit.

All the embodiments of the determination method according to the present disclosure and the advantages of these embodiments apply mutatis mutandis to the present system according to the present disclosure. In particular, this system is efficient, safe and flexible for determining the muscle fatigue.

Preferably, the range of frequencies extends at least on any of the above-mentioned interval of frequencies. Preferably, it extends from 0 to 200 Hz. According to a representative embodiment of the system, the logical unit is configured for:

carrying out a computation on at least some of the forces, among which:
        a first force determined by the device as a force developed by the muscle in response to a first electrostimulation generated by the stimulator at a first frequency of the range of frequencies, and
        a second force determined by the device as a force developed by the muscle in response to a second electrostimulation generated by the stimulator at a second frequency of the range of frequencies, the first frequency being lower than the second frequency and differing from at least 10% of the latter;
    determining the muscle fatigue based on this computation.

Such computation and determination of the muscle fatigue can be performed as described previously.

According to an embodiment of the system, the device comprises at least a strain gauge or a dynamometer for directly measuring the force developed by the muscle in response to an electrostimulation generated by the stimulator. Advantageously, the device allows then for a determination of the forces directly, by measuring directly these forces (in Newton) by means of an appropriate measuring instrument and not by intermediate or indirect measures and/or observations nor deduction or estimation inducing a higher risk of error in the forces determination.

According to a representative embodiment of the system adapted for a muscle of a lower limb of a human as being the muscle, the device is itself a new and dedicated device for determining any force developed by the muscle in response to an electrostimulation generated by the stimulator. This device was already partially described. It comprises:

a seat for receiving the human in a seated position, and adapted for being positioned on a horizontal support;
    a leg support element mechanically coupled to the seat, and adapted for receiving at least part of a leg of the lower limb; and
    measuring instrument for measuring a force developed by the muscle at level of the leg support element, in response to an electrostimulation generated by the stimulator.

The device is configured for remaining substantially stationary with respect to the horizontal support when forces are developed by the muscle at level of the leg support element, in response to the electrostimulations generated by the stimulator at the different frequencies, thanks to a weight of the human exerted at level of the seat.

Advantages of this embodiment of the system were discussed previously. This device is designed to be used without a supervising operator and has a stable and rigid structure so that the forces measurements are precise and reproducible. In particular, the device is simple and light. The device preferably does not comprise back nor leg associated with the seat, so that the seat is substantially planar and can be positioned on any horizontal support such as a table or another seat. The device is then easily transportable and allows forces measurements to be made without the need for additional equipment or structure, wherever the human is. In particular, the human has not to go in a particular medical or sport center for determining the muscle fatigue. The leg support element allows to maintain the part of the leg in position, ensuring precise and reproducible measurements of the force, for instance as it was described. The leg support element preferably comprises a semi-cylindrical hollow portion for conforming to the curvature of the part of a leg while laterally immobilizing this part of the leg. The leg support element can also comprise a strap for better immobilizing the part of the leg. The measuring instrument consists preferentially in a strain gauge or a dynamometer as described above, that can be arranged in the device for working either in traction or in compression, so that reproducible, direct and precise measurements of the forces can be performed.

Preferably, the leg support element of the device is (mechanically) coupled to the seat by a mechanical arm or a mechanical frame. Preferably, the latter comprises a connecting member to the measuring instrument either at level of the seat or at level of the leg support element. Advantageously, the structure of the device is then very simple and light. The arm or the frame can have a simple form, for example a projected form of "I", "L", "T", "U", "S" or "Z" in at least one plane orthogonal to the seat, and preferably comprising at least a high extremity coupled with (or fixed to) the seat, and at least a low extremity coupled with (or fixed to) the leg support element.

Optionally, the device also comprises at least a position adjustment element for modifying at least one among:

a position and/or an orientation of the mechanical arm or the mechanical frame with respect to the seat,
    a position and/or an orientation of the leg support element with respect to the mechanical arm or the mechanical frame.

Such position adjustment element can comprise any mechanical element well known by a person skilled in the art such as a screw, a bolt, a pin, a spring, etc. preferably configured for cooperating with the mechanical arm or frame, for example, within cavities. Preferably, when the mechanical arm or frame is a mechanical arm of a simple form, it comprises such a position adjustment element for orienting the leg support element in one of two opposite senses along a direction (or line) perpendicular to the mechanical arm, one of these senses being adapted for orienting the leg support element adequately for receiving the part of the leg of the human right lower limb, and the other of these senses being adapted for orienting the leg support element adequately for receiving the part of the leg of the human left lower limb. When the mechanical arm or frame is a frame, it preferably comprises such a position adjustment element for positioning the leg support element along a side of the frame adequately for receiving the part of the leg of the human right or left lower limb. The structure of the device is then simple while being adapted to the lower limb to which belongs the muscle of which the muscle fatigue has to be determined.

More specifically, the device of the system consists preferably only in the seat, the leg support element, the measuring instrument, the mechanical arm or the mechanical frame, and any position adjustment element if may comprise. It is then reduced to a very simple and practical form, while allowing to implement step (ii) of the determination method in a very satisfactory way for determining the muscle fatigue.

The disclosed subject matter is further introduced in the claims. As it will be understood by a skilled person from this disclosure, any one of the embodiments presented in the claims can be considered alone or in combination. The dependency of the claims can be considered in a broader manner so that any one of the possible combinations of the claims—as far as they are technically possible and understood by the person skilled in the art, in particular in view of the present disclosure—are part of the present application.

DESCRIPTION OF THE DRAWINGS

Other characteristics and advantages of the disclosed subject matter will appear on reading the following detailed description, for the understanding of which, it is referred to the attached figures where:

FIG. 1 illustrates a flow chart of the determination method according to a representative embodiment of the disclosed subject matter;

FIG. 2 illustrates curves of the (global and/or maximal) force developed by a muscle in response to an electrostimulation at a given frequency as a function of this frequency;

Figure 3:
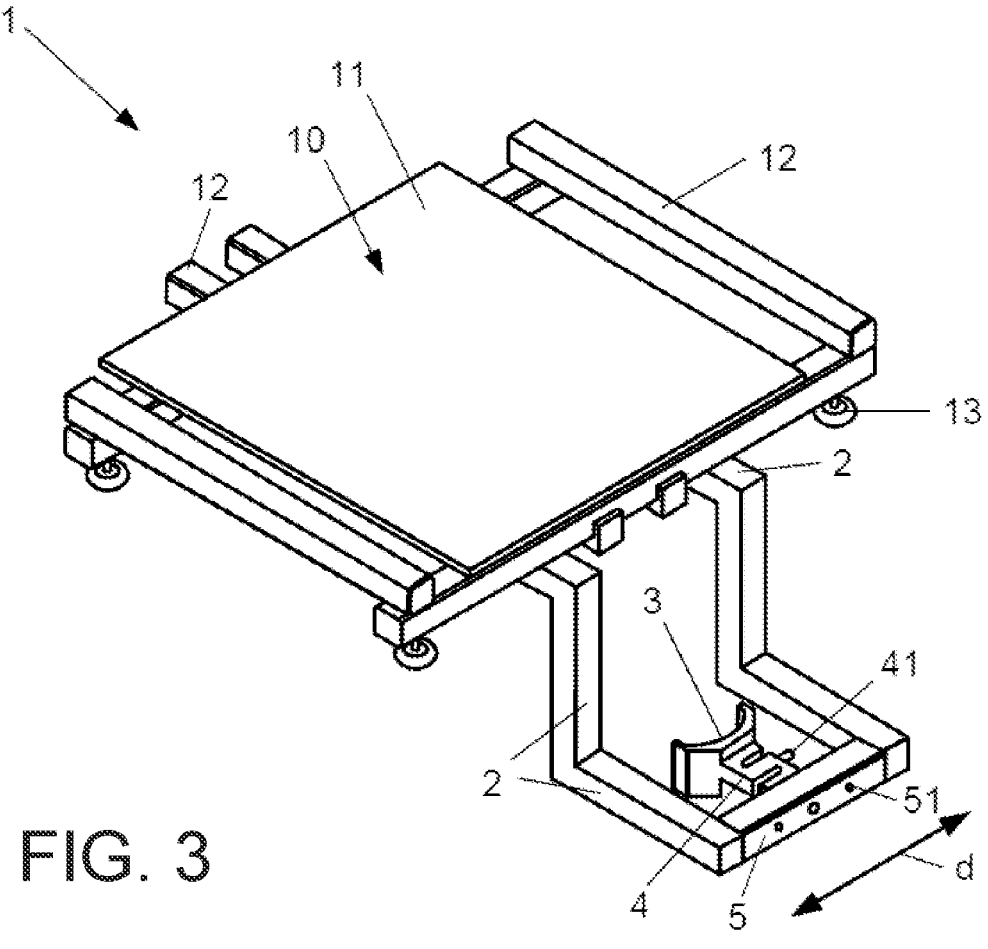
FIG. 3 illustrates a device of a system for implementing a representative embodiment of the muscle fatigue determination method.

The drawings in the figures are not scaled. Similar elements can be assigned by similar references in the figures. In the framework of the present document, identical or analogous elements may have the same references. The presence of reference numbers in the drawings cannot be considered to be limiting, in particular if these numbers are indicated in the claims.

DETAILED DESCRIPTION

Description of representative embodiments of the disclosed subject matter are hereafter described with references to figures, but the present disclosure is not limited by these references. In particular, the drawings or figures described below are only schematic and are not limiting in any way.

As shown in FIG. 1, the illustrated muscle fatigue determination method proposes to electro-stimulate a muscle, at different frequencies $\mu_1, \mu_2, \mu_3, \ldots, \mu_n$, for a number of electrostimulations n, for example $2 \leq n \leq 50$, preferably $2 \leq n \leq 5$, to determine, preferably to measure, the respective (maximal) forces $F_1, F_2, F_3, \ldots, F_n$ developed by the muscle in response to each of the electrostimulations respectively at each frequencies $\mu_1, \mu_2, \mu_3, \ldots, \mu_n$, and to determine a muscle fatigue of the muscle based on the so determined forces $F_1, F_2, F_3, \ldots, F_n$. Such a determination can be performed for example by ratio computation of two forces and/or discrete integral computation, and comparison of at least one of these computations to at least one expected value, as fully explained above.

FIG. 2 illustrates graphs of the (maximal) force developed by the muscle in response to the electrostimulations as a function of the frequency. The force is read on the vertical axis 82 (in Newton), and the frequency is read on the horizontal axis 81 (in Hertz). The curve 61 corresponds to the graph of a theoretical expected function F expressing a force developed by a non-fatigued muscle in response to such electrostimulations as a function of the electrostimulation frequencies. The curve 62 represents a continuous and regular extension of dots cloud corresponding to the points $(\mu_1, F_1), (\mu_2, F_2), (\mu_3, F_3), \ldots, (\mu_n, F_n)$ as measured for a fatigued muscle. It is noticed that the space between the two curves 61 and 62 is greater for low frequencies (e.g. between 10 and 40 Hz), than for high frequencies (e.g. greater than 90 Hz). This space corresponds to differences 71 and 72 between measured forces for the muscle and expected forces from function F for a non-fatigued muscle respectively at low and high frequencies. In particular, the difference 72 is so small that it can be assumed that the two curves 61 and 62 are substantially the same for high frequencies.

If it is assumed that the ratio F(20)/F(120) is known to be about 65%, it is then sufficient to measure the forces $F_1$ and $F_2$ developed by the muscle in response to electrostimulations at $\mu_1=20$ Hz and $\mu_2=120$ Hz respectively for determining the muscle fatigue, advantageously without the need for knowing a specific human dependent curve for the same muscle but non-fatigued.

Indeed, as $F_2$ corresponds substantially to F(120), the measure of $F_2$ corresponds in some sense to a reference measure while the measure of $F_1$ allows to highlight a divergence with expected value in term of ratio to $F_2$.

In particular, when the ratio $F_1/F_2$ differs significantly from 65%, a muscle fatigue is deemed to be determined according to the method, and can be quantified. This value of about 65% for the ratio is indicative and not limitative. Other values such as about 60%, or about 70% or about 80% can be convenient depending on the considered function F. Similarly, these values of $\mu_1$ and $\mu_2$ are completely not limitative. For instance, an identical discussion can be drawn up with $\mu_2=100$ Hz in place of 120 Hz.

An advantageous device 1 for measuring the forces $F_1, F_2, F_3, \ldots, F_n$ for a lower limb muscle is illustrated in FIG. 3. The device is advantageous to implement the muscle fatigue determination method. The device 1 comprises a seat 10 comprising a smooth portion 11 for receiving the human in a seated position, a rigidity frame 12 for the smooth portion 11, and positioning lower members 13 for removable positioning the seat on a horizontal support. The rigidity frame 12 contributes to the rigidity of the seat, in particular at level of the smooth portion 11 which can be made of a flexible and/or padded material for the human comfort. The positioning lower members 13 can be adjustable in height from 0 to $\frac{1}{20}$ meter below the smooth portion 11 for improving the stability of the seat 10 on the horizontal support. They can be suction cups. They can have protected extremities. They are not arranged for being placed on a ground because another part of the device 1 extend much lower than them.

The device 1 comprises a leg support element 3 fixed to the seat 10 by means of a mechanical frame 2 as illustrated. The leg support element 3 includes a semi-cylindrical hollow portion for receiving and at least partially immobilizing a lower part of the lower limb leg. It integrates an measuring instrument 4 for measuring a force developed by the muscle at level of the leg support element 3, in particular in response to the electrostimulations. The mechanical frame 2 comprises a connecting member 5 to the measuring instrument 4 at level of the leg support element. In particular, in the illustrated configuration of FIG. 3, the measuring instrument 4 is a strain gauge fixed along a first direction in sandwich between the leg support element 3 and the connecting member 5. The strain gauge comprises a connecting extremity 41 for connecting the device 1 with a non-represented logical unit of the determination system. The latter is configured for determining a muscle fatigue on basis of at least some of the forces $F_1, F_2, F_3, \ldots, F_n$ determined by the device 1 in response to the electrostimulations at each of the frequencies $\mu_1, \mu_2, \mu_3, \ldots, \mu_n$.

The connecting member 5 also comprises a position adjustment element 51 for changing the position the leg support element 3 and the measuring instrument 4 with respect to the mechanical frame 2, along a second direction d which is perpendicular to the above-mentioned first direction.

It is presented an explicit class of embodiments of the disclosed subject matter. The execution of the method according to such embodiment of the disclosed subject matter comprising the following steps:

for a given initial electric intensity $I_0$ comprised between 10 and 50 mA, preferably of (about) 25 mA, for a given charge step S comprised between 0.1 and 10 mA, preferably of (about) 1 mA, and successively for each integer k between 0 and K (the so called "number of time"), K being comprised between 5 and 30, preferably of (about) 15:

electrostimulating the muscle at a first frequency $\mu_1$ (preferentially of (about) 20 Hz), with a repetition of $N_1$ pulses during a period of time $T_1$ lower than 250 ms, the pulses having a constant duration and an intensity of $I_0+k$ S;

determining a (maximal) force $F_1$ developed by the muscle in response to this electrostimulation;

awaiting for a first rest period $R_1$ comprised between 300 ms and 5 s, preferably of (about) 1 second;

electrostimulating the muscle at a second frequency $\mu_2$ (preferentially of (about) 120 Hz), with a repetition of $N_2$ pulses during a period of time $T_2$ lower than 250 ms, the pulses having a constant duration and an intensity of $I_0+k$ S;

determining a (maximal) force $F_2$ developed by the muscle in response to this last electrostimulation;

determining at least one muscle data information, preferably a muscle fatigue of the muscle, on basis of the determined forces $F_1$ and $F_2$;

awaiting for a second rest period $R_2$ comprised between 330 ms and 10 s, preferably of (about) 5 seconds.

It can be noticed that the formula $T_1=N_1/\mu_1$ and $T_2=N_2/\mu_2$ makes the links between the number of pulses, the time duration of an electrostimulation and the frequency of electrostimulation. In particular, preferably, $N_1$ is (about) 5 for $\mu_1$ being (about) 20 Hz and $N_2$ is (about) 18 for $\mu_2$ being (about) 120 Hz. These number of pulses allows to reach maximal forces $F_1$ and $F_2$ while allowing the electrostimulation times $T_1$ and $T_2$ to be bounded by 250 ms to avoid voluntary perturbation of the forces measurements. For example, if it is considered $N_2$ as being 25, $T_2$ is still below 250 ms, but the (maximal) force $F_2$ will remain substantially unchanged in comparison to the one for $N_2$ being 18. These values of $N_1$ and $N_2$ were in particular experimentally derived by the inventors as a suitable embodiment of the disclosed subject matter associated to the above-mentioned values of $\mu_1$ and $\mu_2$.

Figure 4:
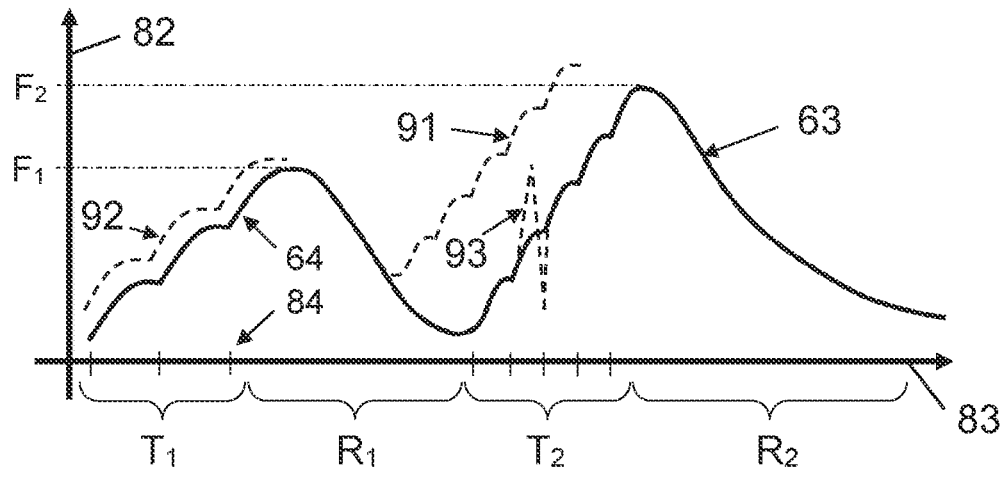
FIG. 4 illustrates schematic experimental curves of forces measured in function of time during an execution of the method according to a representative embodiment of the disclosed subject matter.

FIG. 4 illustrates a purely schematic curve 63 of (contraction) forces developed of a human lower limb muscle in function of time during part of an execution of the method according to such an embodiment of the disclosed subject matter. In particular, this figure illustrated the electrostimulation effects for an arbitrary k, comprising then a whole execution of step (i). It can easily be derived that the curve repeat similarly itself after the second rest period $R_2$ for each occurrence of step (i), i.e. for each k. The notations $T_1$, $R_1$, $F_1$, $T_2$, $R_2$, $F_2$ introduced above apply similarly to FIG. 4.

The graph of FIG. 4 is distinct from the one of FIG. 2 expressing only the maximal force determined at step (ii) for each frequency. The curve 63 is based on experimental measurements and reproduced in a schematic way. The measured forces (e.g. by a strain gauge) is still read on the vertical axis 82 (in Newton), but the horizontal axis 83 indicates now the time. FIG. 4 is schematic and do not represent explicit experimental data. The axis are not necessarily endowed with a linear scale. In particular, for the present sake of clarity the numbers $N_1$ and $N_2$ corresponding to the illustration of FIG. 4 are respectively 3 and 5, and the periods of time $T_1$, $R_1$, $T_2$ and $R_2$ noted on axis 83 are not proportionally scaled.

It is visible on FIG. 4 that the muscle is electro-stimulated at the first frequency $\mu_1$, with a repetition of 3 pulses during a period of time $T_1$ lower than 250 ms, the pulses having a constant duration and an intensity of $I_0+k$ S. Each pulses generation corresponds to a bar 84 on the time axis 83. The effect of the pulses on the curve 63 is noted by 64 and is clearly visible as a contraction of the muscle, and then a progressive increase of the force developed by the muscle by a muscular tetanic process. In other words, as the pulses generated 84 are close enough, a kind of fusion of the muscular effect of each individual pulse is observed along the period of time $T_1$, providing then such a staircase shaped portion of the curve 63 above the period of time $T_1$.

The same discussion applies for the electrostimulation of the muscle at step (i) at the second frequency $\mu_2>\mu_1$, with a repetition of 5 pulses during a period of time $T_2$ lower than 250 ms, the pulses having the same constant duration and intensity of $I_0+k$ S.

Each of these electrostimulations at frequencies $\mu_1$ and $\mu_2$ during the respective periods of time $T_1$ and $T_2$ allows to reach and determine a maximal force, respectively $F_1$ and $F_2$, developed by the muscle in response to the electrostimulation, as it is visible on axis 82 of FIG. 4, and consecutively to determine a muscle fatigue at step (iii). As it is visible on FIG. 4, the first and second rest periods $R_1$ and $R_2$ are long enough to allow the muscle to return to "normal" and/or "relaxed" conditions, without any contraction or residual force developed due to the preceding electrostimulation, and this before the beginning of the next electrostimulation. In other words, the rest periods $R_1$ and $R_2$ allow the curve 63 to return to a baseline. The rest period $R_1$ occurs between the electrostimulations at the frequencies $\mu_1$ and $\mu_2$ with the same pulse intensity of the form $I_0+k$ S. The rest period $R_2$ occurs between the electrostimulation at the frequency $\mu_2$ with a pulse intensity $I_0+k$ S and the electrostimulation at the frequency $\mu_1$ with a pulse intensity $I_0+(k+1)$ S.

As widely explained in the present disclosure, this method is convenient for avoiding disturbance effects on the determination of the forces $F_1$ and $F_2$. FIG. 4 illustrates also in dot lines examples of effects of such disturbances 91, 92 and 93 on the curves 63. Those are purely fictional as the method is specifically conceived for avoiding them.

Disturbance 91 shows an example of a tetanic effect on the curve 63 due to a non-respect of the above discussed lower bounds for the first rest period $R_1$. If this period does not last enough, the muscle is still contracted and not relaxed when the next electrostimulation starts, which affects the measure of $F_2$ as being too high due to the partial (tetanic) fusion of the effect of the electrostimulations at the frequencies $\mu_1$ and $\mu_2$. If the fusion is partial and very limited (i.e. for $R_1$ greater than 115 ms), it is nevertheless possible to apply a direct mathematical treatment (e.g. by linear interpolation) to determine force $F_2$ from the observed disturbed curve 91. A similar discussion can obviously apply for the second rest period $R_2$.

Disturbance 92 shows an example of a potentiation effect on the curve 63, above the time period $T_1$ (but the skilled person would easily understand that such effect is not limited above this time period). By not increasing the pulse intensity by a charge step S between consecutive occurrences of step (i), the muscle becomes potentiated, and then the real force $F_1$ is disturbed, in particular higher than it should, due to a kind of training of the muscular fibers. The increasing of the intensity between consecutive occurrences of step (i) according to the present disclosure allows to avoid such potentiation effect.

Finally, disturbance 93 shows an example of a voluntary and/or reflex muscular contraction by the subject in parallel to an electrostimulation. The subject increases the force at a pulse generation and decreases it between or after the pulses. Advantageously, such disturbance cannot occur given that the time periods $T_1$ and $T_2$ are so short (at most 250 ms) than the subject cannot react by himself during an electrostimulation.

It will be easily understood by the skilled person that the number n of electrostimulations for the class of embodiments is equal to 2, but that these embodiments can easily be generalized to any number n>1.

In other words, the present disclosure relates to a determination method of a muscle fatigue based on information arising from forces developed by the muscle in response to electrostimulations of the latter at different frequencies during a limited period of time-preferably lower than 5 s.

The disclosed subject matter has been described in relation to the specific embodiments which have a value that is purely illustrative and should not be considered to be limiting. The skilled person will notice that the disclosed subject matter is not limited to the examples that are illustrated and/or described here above. The disclosed subject matter comprises each of the new technical characteristics described in the present document, and their combinations. The embodiments and advantage of the determination method applies mutatis mutandis to the aforementioned sport activity planning method.

The invention claimed is:

1. A method for determining a muscle fatigue of a muscle that includes the step of:

(i) electrostimulating the muscle by:

(i-a) selecting a first frequency between 0 and 500 Hz;

(i-b) inducing the muscle to develop a maximal force by stimulating the muscle with a stimulator configured to apply a series of electrical pulses at the first frequency ending after less than 500 ms;

(i-c) providing a first rest period during which the muscle is allowed to return to a condition without any contraction or residual developed forces, the rest period having a duration between 100 ms and 10 s during which the muscle is not stimulated;

(i-d) increasing the first frequency to a second frequency, wherein a difference between the first frequency; and the second frequency is at least 10% of the second frequency; and (i-e) repeating steps (i-b) through (i-c) at least one time;

(ii) measuring forces developed by the muscle in response to the electrostimulations of step (i) by a measuring instrument; and (iii) determining a muscle fatigue on basis of the forces measured at step (ii);

wherein a duration of the electrostimulation at step (i) is limited for each frequency so as to avoid muscle voluntary or reflex disturbance.

2. The method according to claim 1, wherein the stimulation at step (i-b) comprises repetition of pulses during more than 150 ms and less than 250 ms.

3. The method according to claim 1, wherein, for each frequency, the pulses are repeated between 5 and 20 times.

4. The method according to claim 1, wherein the duration of the first rest period is between 300 ms and 1 s.

5. The method according to claim 1, wherein, the step of electrostimulating at step (i) is performed at a given electric charge, and wherein the method further comprises the step of:

(iv) repeating steps (i), (ii) and (iii) a number of times with increasing electric charge, the electric charge at step (i) being increased by a charge step between two occurrences of step (i).

6. The method according to claim 5, wherein the electric charge is defined by an electric intensity of the pulses or a pulse duration.

7. The method according to claim 6, wherein the electric intensity for a constant pulse duration is increased between 10 and 100 mA, the number of times being comprised between 5 to 30, and the charge step being an intensity increasing comprised between +0.1 and +10 mA.

8. The method according to claim 7, wherein the electric intensity is increased from 25 to 40 mA with 15 charge steps of +1 mA.

9. The method according to claim 5, wherein a second rest period having a duration between 100 ms and 5 minutes occurs between two occurrences of step (i).

10. The method according to claim 9, wherein the duration of first rest period is less than the duration of second rest period.

11. The method according to claim 9, wherein the duration of the second rest period is between 145 ms and 10 s.

12. The method according to claim 1, comprising, before step (i), a preliminary step of electrostimulating the muscle with an isolated pulse, and wherein a third rest period having a duration between 100 ms and 10 s occurs between the preliminary step and step (i).

13. The method according to claim 1, the forces comprise a first force developed by the muscle in response to the electrostimulation of step (i) at the first frequency, and a second force developed by the muscle in response to the electrostimulation of step (i) at the second frequency.

14. The method according to claim 13, wherein the first frequency is between 0 and 50 Hz and the second frequency is between 50 and 200 Hz.

15. The method according to claim 14, wherein step (i) comprises:

when the frequency is the first frequency, electrostimulating the muscle with a repetition of 3, 4, 5, or 6 pulses at the first frequency of 10, 15, 20 or 25 Hz during a first period of time having a duration between 100 and 250 ms; and when the frequency is the second frequency, electrostimulating the muscle with a repetition of 16, 17, 18 or 19 pulses at the second frequency of 100, 110, 120 or 130 Hz during a second period of time having a duration between 100 and 250 ms.

16. The method according to claim 1, wherein step (iii) comprises a comparison of the forces determined at step (ii), and a determination of the muscle fatigue based on this comparison of the forces.

17. The method according to claim 13, wherein step (iii) comprises a computation of a ratio of the first force to the second force, a comparison of the computed ratio to a threshold, and a determination of the muscle fatigue based on the comparison of the computed ratio to the threshold.

18. The method according to claim 1, wherein the measuring instrument comprises at least one of a strain gauge and a dynamometer.

19. The method according to claim 1, comprising, before step (i):

(a) providing a device comprising:

a seat configured to receive a human in a seated position and adapted to be positioned on a horizontal support;

a leg support element mechanically coupled to the seat and adapted to receive at least part of a leg of a lower limb; and the measuring instrument, the measuring instrument being configured to measure the forces at level of the leg support element;

(b) positioning the seat on the horizontal support;

(c) positioning the human on the seat, in a seated position; and (d) positioning at least part of the leg on the leg support element, wherein the forces are measured at step (ii) by the measuring instrument, and the device remains substantially stationary with respect to the horizontal support during an execution of steps (i) and (ii) in response to a weight of the human exerted at level of the seat.

20. A method for planning a sport activity, comprising the following steps:

(0) identifying a muscle to be stimulated during the sport activity;

(1) executing the method according to claim 1 for determining a muscle fatigue of the muscle identified at step (0); and (2) planning the sport activity on a basis of the muscle fatigue determined at step (1).

21. The method according to claim 1, wherein step (ii) further comprises using a computer configured to apply a treatment to forces measured by the measuring instrument to delete disturbances prolonging the muscular response from an electrostimulation at a frequency to another electrostimulation at another frequency at step (i).

* * * * *